(12) United States Patent
Le Dimet et al.

(10) Patent No.: US 11,939,099 B2
(45) Date of Patent: *Mar. 26, 2024

(54) DEVICE FOR VACUUM STOPPERING A MEDICAL CONTAINER

(71) Applicant: Becton Dickinson France, Le Pont de Claix (FR)

(72) Inventors: Gwenn Le Dimet, Charavines (FR); Julien Gagliano, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/876,155

(22) Filed: Jul. 28, 2022

(65) Prior Publication Data

US 2022/0363424 A1 Nov. 17, 2022

Related U.S. Application Data

(63) Continuation of application No. 16/629,692, filed as application No. PCT/EP2018/068738 on Jul. 11, 2018, now Pat. No. 11,434,033.

(30) Foreign Application Priority Data

Jul. 11, 2017 (EP) ..................................... 17305912

(51) Int. Cl.
*B65B 67/02* (2006.01)
*A61M 5/31* (2006.01)
(Continued)

(52) U.S. Cl.
CPC ............... *B65B 67/02* (2013.01); *A61M 5/31* (2013.01); *B65B 7/2821* (2013.01);
(Continued)

(58) Field of Classification Search
CPC .......... A61M 2207/00; A61M 2207/10; A61M 5/31; B65B 31/027; B65B 31/047;
(Continued)

(56) References Cited

U.S. PATENT DOCUMENTS 4,186,542 A * 2/1980 Oyagi ....................... B67B 1/04
53/109
4,848,419 A * 7/1989 Damen ................. B65B 31/046
141/61
(Continued)

FOREIGN PATENT DOCUMENTS

CN 209405397 U 9/2019
DE 19909995 A1 9/2000
(Continued)

*Primary Examiner* — Andrew M Tecco
*Assistant Examiner* — Nicholas E Igbokwe
(74) *Attorney, Agent, or Firm* — The Webb Law Firm

(57) ABSTRACT

The invention relates to a device for vacuum stoppering a medical container. The device includes a main body defining an internal volume that has a variable pressure chamber configured to be connected to a vacuum pump. A stopper holder system is arranged in communication with the variable pressure chamber and is configured to receive and hold a stopper aligned with the direction of travel of a piston rod. A piston rod is moveable inside the internal volume of the main body along a longitudinal axis between a proximal rest position and a distal operative position wherein the piston rod pushes the stopper into the medical container. A container holder system provided in the main body, is arranged distally relative to the stopper holder system and in communication with the variable pressure chamber.

22 Claims, 7 Drawing Sheets

(51) Int. Cl.
*B65B 7/28* (2006.01)
*B65B 31/02* (2006.01)
*B65B 31/04* (2006.01)
*B65B 59/00* (2006.01)

(52) U.S. Cl.
CPC .......... *B65B 31/027* (2013.01); *B65B 31/047* (2013.01); *B65B 59/003* (2019.05); *A61M 2207/00* (2013.01); *A61M 2207/10* (2013.01)

(58) Field of Classification Search
CPC ....... B65B 59/003; B65B 67/02; B65B 7/161; B65B 7/2821
See application file for complete search history.

(56) References Cited

U.S. PATENT DOCUMENTS

| | | | |
|---|---|---|---|
| 5,256,154 A | | 10/1993 | Liebert et al. |
| 10,266,293 B1 | * | 4/2019 | Russell ................. B65B 7/2828 |
| 2010/0218846 A1 | * | 9/2010 | Kriheli .................. A61J 1/2096 |
| | | | 141/5 |
| 2015/0190578 A1 | * | 7/2015 | Okihara .................. A61M 5/28 |
| | | | 53/432 |
| 2016/0058667 A1 | * | 3/2016 | Kriheli ...................... A61J 1/22 |
| | | | 604/414 |

FOREIGN PATENT DOCUMENTS

| | | | | |
|---|---|---|---|---|
| GB | 2322851 A | * | 9/1998 | ........... B65B 31/027 |
| GB | 2322851 A | | 9/1998 | |
| RU | 2093194 C1 | | 10/1997 | |
| WO | 2019011961 A1 | | 1/2019 | |

* cited by examiner

DEVICE FOR VACUUM STOPPERING A MEDICAL CONTAINER

CROSS-REFERENCE TO RELATED APPLICATIONS

This application is a continuation of U.S. patent application Ser. No. 16/629,692 filed Jul. 11, 2018, which is the United States national phase of International Application No. PCT/EP2018/068738 filed Jul. 11, 2018, and claims priority to European Patent Application No. 17305912.2 filed Jul. 11, 2017, the disclosures of which are hereby incorporated by reference in their entirety.

BACKGROUND OF THE INVENTION

Field of the Invention

The invention relates to a device for stoppering a medical container as a syringe or the like using vacuum, a system for stoppering a medical container comprising such a device, and a method for stoppering a medical container using vacuum with such a device or system.

Description of Related Art

Prefilled injection devices are common containers to deliver drugs or vaccines to patients and include syringes, cartridges and autoinjectors or the like. They usually comprise a sealing stopper in gliding engagement into a container, the container being filled with a pharmaceutical composition in order to provide the practitioners with a ready-to-use injection device for patients.

A container has a substantially cylindrical shape, and comprises a proximal end able to be stoppered by a sealing stopper, a distal end wherein the pharmaceutical composition is expelled from the container, and a lateral wall extending between the proximal end and the distal end of the container. In practice, the sealing stopper is aimed at moving, upon the pressure exerted by a plunger rod, from a proximal end of the container body towards the distal end of the container body, thereby expelling the drug contained into the container body.

When compared to empty injection devices that are filled with a vial-stored pharmaceutical composition just prior to the injection to the patient's body, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers may encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical product thus reducing buying and supply chain costs.

Prefilled injection devices are usually obtained by filling an empty medical container with a desired pharmaceutical composition, then stoppering the filled container under vacuum or by vent tube or a combination of both.

The term "vacuum" used herein means a low pressure, far inferior to the atmospheric pressure of 1013.25 hectoPascal (hPa) (equals to 1.013 bar), and preferably close to 0 hPa.

A filled container is generally stoppered right after filing of the drug into the container body using stoppering machines according to the following method: the medical container to be stoppered is positioned on an adapted support (for example, in a nest or clipped directly on the stoppering machine), with its proximal end up, that is with its distal end down and maintained in this position.

In the case of vent tube stoppering, the stopper is compressed in a tube, usually called "vent tube", which outer diameter is smaller than the inner diameter of the container, so as to allow air circulation between the vent tube and the container before the stopper is positioned into the container.

In the case of vacuum stoppering, a suction cup in communication with a variable pressure chamber is then positioned onto the distal end of the container so as to close it in a tight manner. At this time, the pressure inside the variable pressure chamber and the pressure in the portion of the medical container above the composition are both substantially equal to the atmospheric pressure $P_0$. The variable pressure chamber is connected to a vacuum pump or the like and placed under vacuum. As a result, the variable pressure chamber and the pressure in the portion of the medical container above the composition are both under vacuum, at a pressure $P_1$, inferior to the initial pressure $P_0$. A sealing stopper, previously positioned inside the chamber, is then moved by a piston rod to the proximal end of the container above the composition. The breaking of the vacuum inside the variable pressure chamber then causes the stopper to move further down the medical container until equilibrium of pressure: the medical container is then stoppered.

The main advantage of this method of stoppering medical containers under vacuum is that the remaining bubble inside the stoppered container, resulting from a small volume of air remaining between the stopper and the surface of the composition, is therefore rendered as small as possible. In addition, due to the small compression of the stopper, less constraint is applied to the stopper, which leads to fewer defects, specifically on coated stoppers.

This method is carried out using large and heavy machines thus implying the following drawbacks.

Lab scale machines that are commonly used in this field cannot be sterilized. Indeed, these machines are not easily movable by an operator and cannot be placed in an autoclave due to their dimensions, weight and design. They also include electrical and electronic parts that are not autoclavable.

Moreover, as the process of vacuum stoppering medical containers is generally carried out in clean rooms to ensure the sterility of the medical containers, therefore, the corresponding equipment has to be placed in the clean rooms as well.

The performance of quick and simple implementation of vacuum stoppering of a medical container, which do not necessarily require to be carried out in sterile conditions, thus have to be carried out in a clean room anyway, as the machines cannot be moved from said clean rooms. For example, small scale aseptic filling can be carried out in reduced sterile environment such as under laminar flow hood. Such small environment does not allow the placement of heavy stoppering equipment due to their dimensions, weight, and the fact that they cannot be sterilized.

Yet operating in a clean room is very constraining for an operator, who has to get dressed accordingly and observe strict and specific work procedures, thus renders implementation of the vacuum stoppering much longer and demanding to carry out.

As a consequence, there is a strong need for a device for vacuum stoppering a medical container that is, at the same time, sterilizable and easily and rapidly movable from one place to another so as to be used with no restriction of area, and that can be used outside clean rooms.

In addition, there is also a need for a device that is easy to use, allowing the performance of quick and simple implementation of vacuum stoppering of a medical container, in particular prior to a clinical trial involving the use of an injection device comprising such a medical container.

SUMMARY OF THE INVENTION

An object of the invention is thus to provide a device for vacuum stoppering a medical container that overcomes the drawbacks of the known devices.

Such an improved device is sterilizable and easily and rapidly movable, and can be used with no restriction of area.

The device allows the performance of quick and simple implementation of vacuum stoppering of a medical container, in particular prior to a clinical trial involving the use of an injection device comprising such a medical container.

One object of the invention is a device for vacuum stoppering a medical container, comprising:
- a main body defining an internal volume that comprises a variable pressure chamber configured to be connected to a vacuum pump;
- a stopper holder system arranged in communication with the variable pressure chamber and configured to receive and hold a stopper in a fixed position relative to the main body and aligned with the direction of travel of a piston rod;
- a piston rod moveable inside the internal volume of the main body along a longitudinal axis between a proximal rest position wherein the piston rod is remote from the stopper and a distal operative position wherein the piston rod contacts and pushes the stopper into the medical container;
- a container holder system provided in the main body, arranged distally relative to the stopper holder system and in communication with the variable pressure chamber, said container holder system being configured to receive the proximal end of a medical container to be stoppered and to hold the medical container aligned with the direction of travel of the piston rod so that when moving, the piston rod pushes the stopper from the stopper holder system into the medical container to stopper the medical container.

In this application, the "distal direction" is to be understood as meaning the direction of introduction of the stopper into the medical container, and the "proximal direction" is to be understood as meaning the opposite direction to said direction of introduction of the stopper into the medical container.

According to other optional features of the device of the invention:
- the main body comprises a first portion including a spacer configured to guide the piston rod along the longitudinal axis, and a second portion distally adjacent to the first portion, including the variable pressure chamber, the stopper holder system, and the container holder system;
- the first portion and the second portion are configured to be selectively connected to each other or separated from each other;
- the first portion and the second portion are preferentially connected by a threaded connection or a snap-fit connection. The first portion and the second portion can alternatively be connected by other suitable connections, provided that sufficient tightness can be achieved, for example with further positioning of a seal on the connection;
- the main body comprises at least two second portions, each comprising a container holder system configured to receive an end of a medical container of a different size;
- the container holder system comprises:
  - a proximal wall provided with an opening in communication with the variable pressure chamber, the opening being aligned with the longitudinal axis of the piston rod and configured so that, when pushing on the piston rod, said piston rod passes through the opening,
  - a distal wall facing the proximal wall and joined to the proximal wall by a lateral wall provided with a slot, the distal wall being provided with a through groove continuous with the slot and extending in the distal wall from the slot,
  the proximal wall, the distal wall, and the lateral wall defining a housing in-between able to receive the end of the medical container inserted through the slot and moved along the groove to be aligned with the direction of travel of the piston rod;
- the proximal wall of the container holder system comprises a recess provided with the opening, the recess being configured to contact the end of the medical container and to block the medical container radially when the medical container is positioned in the housing and when the variable pressure chamber is under vacuum;
- the container holder system is configured so that, when the container is received in the container holder system, the proximal end of the container faces and contacts axially a surface of the container holder system. In that way, the surface of the container holder system closes the proximal end of the container, thereby providing an effective sealing of the device by avoiding any air leak between the device and the environment;
- the stopper holder system is configured to maintain the stopper both axially and radially;
- the stopper holder is configured to compress the stopper radially;
- the stopper holder is configured to compress the stopper radially, while allowing air to circulate through the stopper holder;
- the stopper holder system comprises a plurality of blocking elements having a curved surface, the curved surface being configured to compress the stopper radially;
- the stopper holder system comprises a plurality of blocking elements arranged as a crown, the stopper holder system being arranged so that when moving, the piston rod passes through the center of the crown to push the stopper away from the blocking elements;
- the blocking elements are advantageously mushroom-shaped, each blocking element comprising a stem topped by an enlarged head, and each blocking element being connected to an adjacent one by a circular wall forming the wall of the crown, so that when in position in the stopper holder system, the stopper is in contact with the stems of the blocking elements and blocked in the proximal direction, with respect to the direction of travel of the piston rod from the rest position to the operative position, by the heads of the blocking elements, and the stopper defines, with the blocking elements and the wall of the crown, a plurality of air-circulating passages;

the stopper holder system comprises advantageously two sets of blocking elements, the respective blocking elements of the two sets being arranged as two concentric crowns wherein each blocking element is connected to an adjacent one by a circular wall that forms the wall of the each crown, and:
- the blocking elements of the first set form angular parts that extend radially from the wall of the first crown,
- the blocking elements of the second set form bearing parts that extend radially from the wall of the second crown, each bearing part including at least one perforation;
- the blocking elements of the two sets are configured so that when in position in the stopper holder system, the stopper is in contact with an apex of the angular parts and blocked in a distal direction, by the bearing parts, and the perforations of said bearing parts are configured for air circulation between the chamber and the container;

the piston rod comprises a handle so as to be moved manually by a user;

the device is handheld, i.e. can be carried in one hand of a user during use and transport from one location to another. The dimensions and the weight of the device are advantageously adapted for this purpose.

Another object of the invention is a system for vacuum stoppering a medical container comprising a device as described above. According to a preferred embodiment, the system comprises a vacuum pump and a vacuum valve for pulling vacuum and adjusting the pressure in the variable pressure chamber of the device to a pressure $P_1$ inferior to the atmospheric pressure $P_0$, and a back valve for breaking vacuum so as to adjust the pressure in the variable pressure chamber back to the atmospheric pressure $P_0$. The system advantageously comprises and a digital display associated with a probe positioned inside the variable pressure chamber so as to measure and display the pressure in the variable pressure chamber for an operator.

Another object of the invention is a method for vacuum stoppering a medical container using a device or a system as described above. The method comprises the elements of:
a) Positioning a stopper in the stopper holder system;
b) Positioning a medical container pre-filled with a composition in the container holder system;
c) Pulling vacuum in the variable pressure chamber so as to decrease the pressure inside the variable pressure chamber;
d) Moving the piston rod to the operative position so as to position the stopper inside the medical container, when the pressure is down to a desired level;
e) Breaking the vacuum so as to increase the pressure inside the variable pressure chamber, causing the stopper to move further down the medical container to the surface of the composition.

Advantageously, for carrying out the method, the device is held in a user's hand, and at least elements a), b), and d) are carried out manually by the user.

BRIEF DESCRIPTION OF THE DRAWINGS

Further features and advantages of the invention will become apparent from the detailed description to follow, with reference to the appended drawings, in which.

DESCRIPTION OF THE INVENTION

Figure 1:
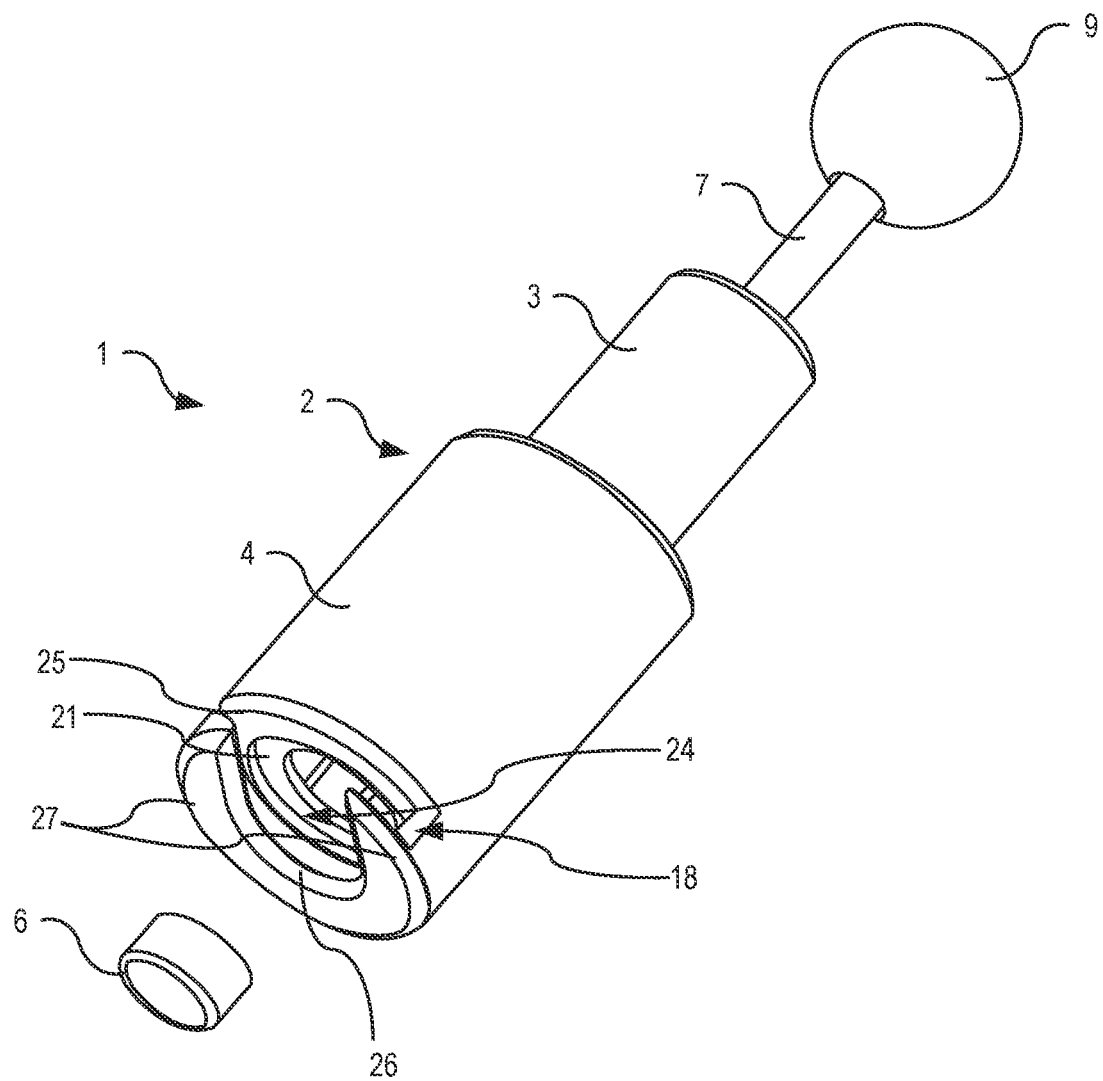
FIG. 1 is a perspective view of an embodiment of the device of the invention.

The invention proposes a device 1 for vacuum stoppering a medical container 28, said device being easy to use and to move. In particular, the device 1 can be handled by an operator to perform quick and simple implementation of vacuum stoppering of a medical container 28 readily.

The device 1 comprises a main body 2, a stopper holder system 12 adapted to maintain a stopper 6 in a fixed position prior to its positioning into a container 28 to be stoppered, a piston rod 7 movable inside the main body 2 along a longitudinal axis (A) for positioning the stopper 6 into the proximal end of the container 28 to be stoppered, and a container holder system 18 adapted to maintain the container 28 in a fixed position aligned with the longitudinal axis (A) of travel of the piston rod.

According to the embodiment of FIG. 1, the main body 2 of the device has a substantially cylindrical shape, and comprises a first portion 3 and a second portion 4 distally adjacent to the first portion. Both first and second portions of the main body 2 define an internal volume delimited by their lateral walls and the first portion 3 has preferably a smaller diameter than the one of the second portion 4.

The main body 2 comprises in the second portion 4 a variable pressure chamber 5 located inside the internal volume. The variable pressure chamber 5 is configured to be connected to a vacuum pump 30 (as visible on FIG. 4) or the like via an outlet 36 provided in the corresponding part of the lateral wall of second portion 4 of the main body 2. The pressure inside the variable pressure chamber 5 thus can be modified, in particular decreased below the atmospheric pressure so that the variable pressure chamber 5 is under vacuum.

Figure 2A:
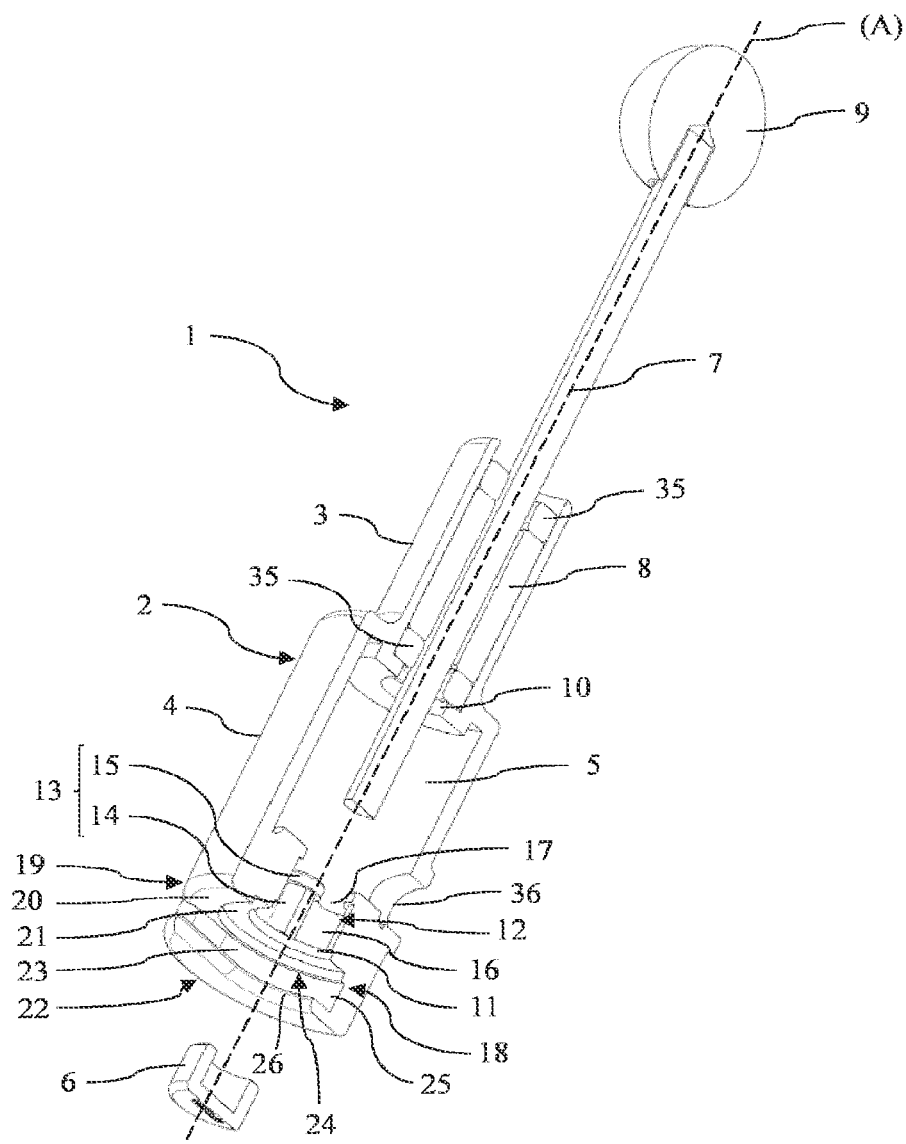
FIGS. 2A, 2B, 2C are three sectional perspective views of the device illustrated in FIG. 1 according to three different positions of the piston rod.
Figure 2B:
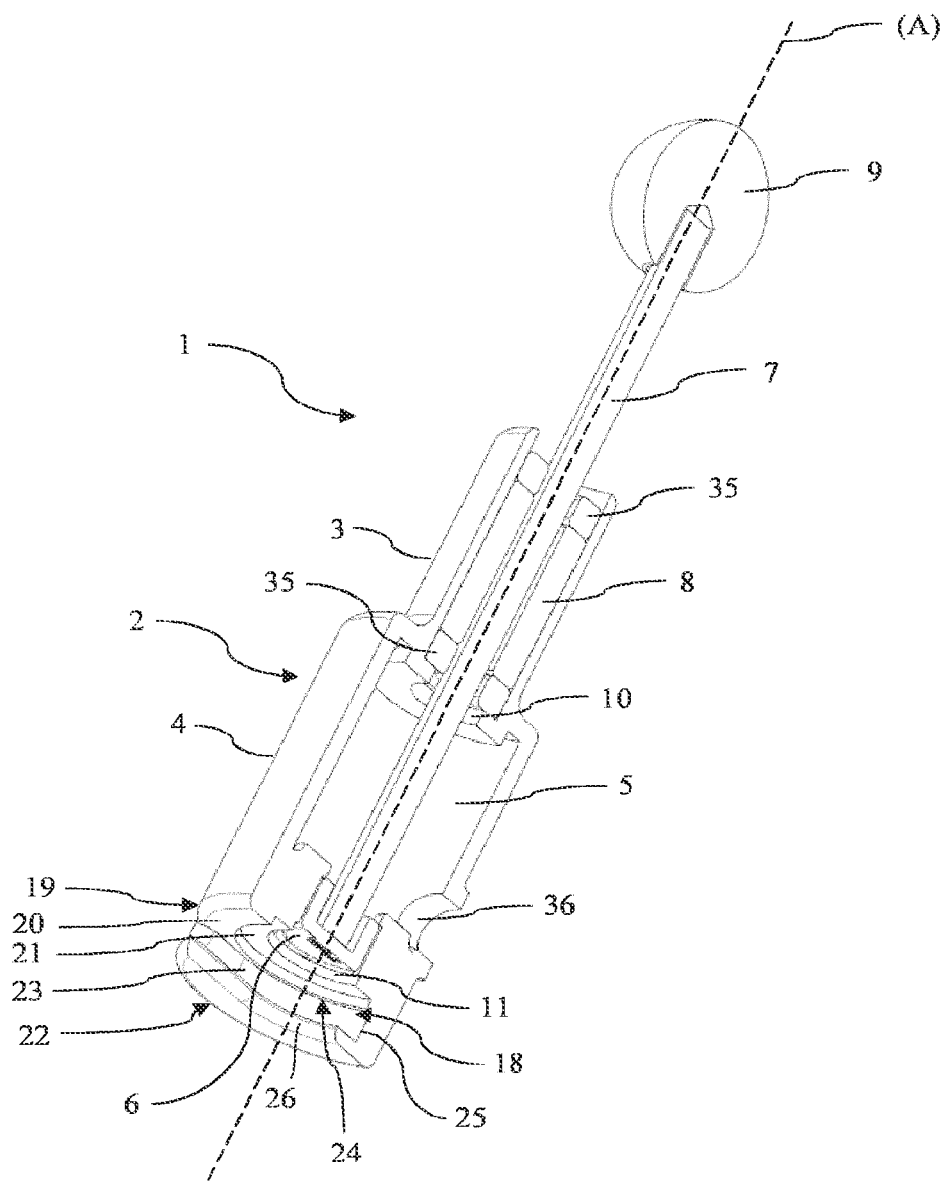
Figure 2C:
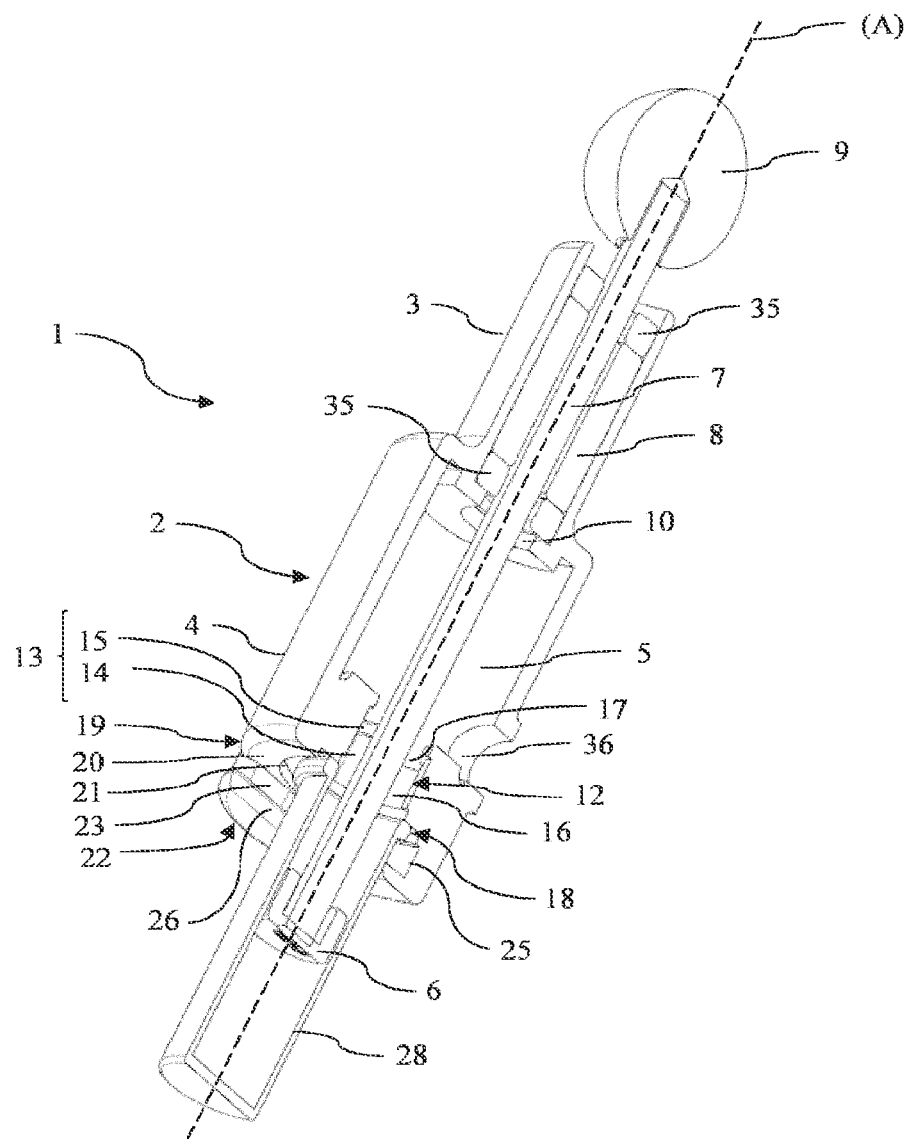
Figure 3:
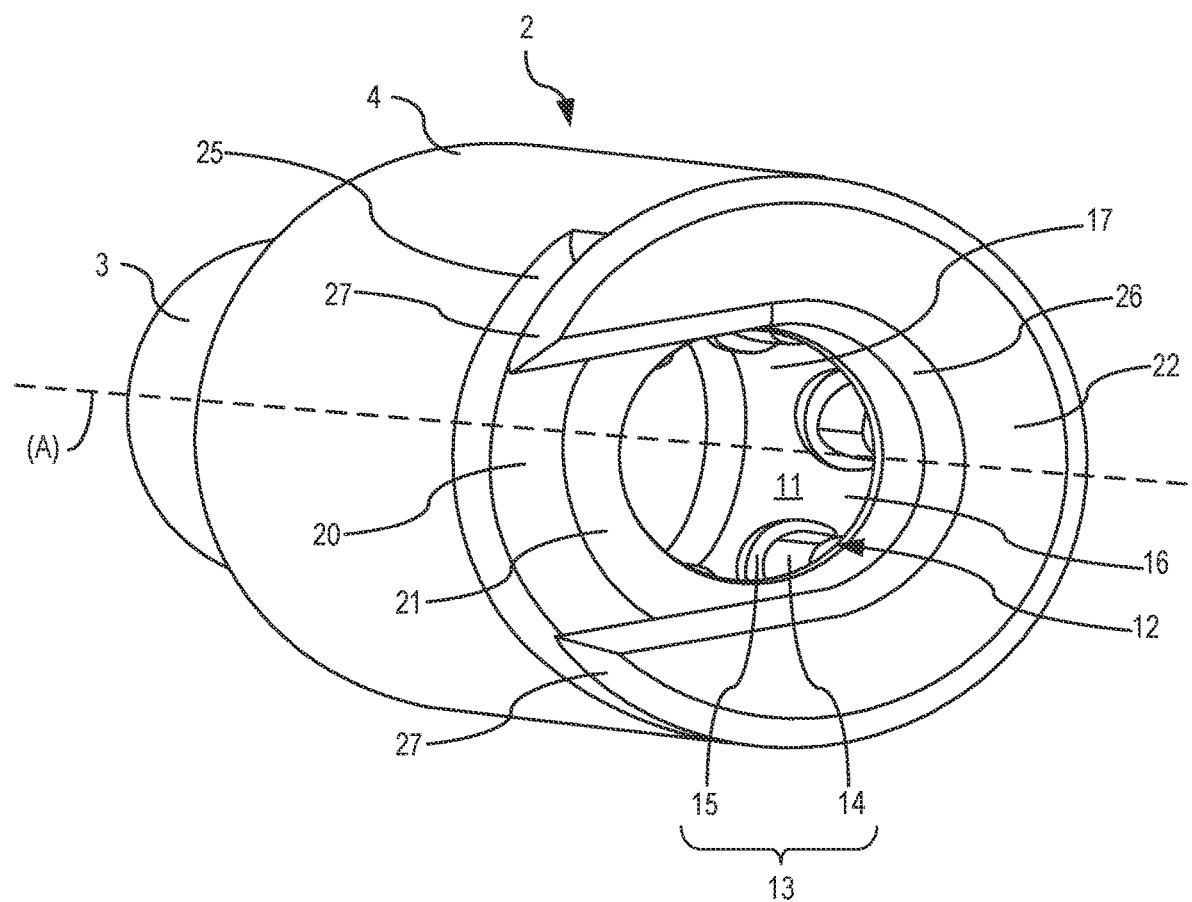
FIG. 3 is a perspective view of an embodiment of the stopper holder system of the device.

According to FIGS. 2A, 2B, and 2C, the piston rod 7 of the device extends along the longitudinal axis (A) and is moveable inside the internal volume of the main body 2 along the longitudinal axis (A), from the first portion 3 of the main body 2 to the second portion 4 of the main body, and vice versa. In the embodiment of FIG. 1, the longitudinal axis (A) of the piston rod 7 corresponds to the revolution axis of the device 1 around which revolves the main body 2. In particular, the piston rod 7 is moveable through the variable pressure chamber 5 along the longitudinal axis (A) and crosses a first opening 10 and a second opening 11 of the main body 2, respectively located at the proximal and distal ends of the second portion 4 of the main body 2.

The direction of travel of the piston rod 7 along the axis (A) from the first portion 3 to the second portion 4 of the main body is referenced as the "distal direction", whereas the direction of travel of the piston rod 7 along the axis (A) from the second portion 4 to the first portion 3 of the main body 2 is referenced as the "proximal direction"

In more details, the piston rod 7 is movable, when pushed by a user, between a rest position illustrated in FIG. 2A wherein the distal end of the piston rod is located in the chamber 5, in the vicinity of the first opening 10 between the two portions 3, 4 of the main body 2, and an operative position illustrated in FIG. 2C wherein the distal end of the piston rod 7 contacts the stopper 6 and pushes said stopper into the container 28 positioned in the container holder system 18 prior to the travel of the piston rod. The position of the piston rod 7 illustrated in FIG. 2B corresponds to an intermediate position wherein the distal end of the piston rod 7 contacts the stopper 6 prior to pushing said stopper in a distal direction.

In order to facilitate the understanding of the present text, the positioning of the elements constituting the device 1 will be described in reference to the proximal or distal directions of travel of the piston rod 7 as described above.

The piston rod 7 is driven along the axis (A) by a spacer 8 located in the first portion 3 of the device 1.

The spacer 8 communicates with the variable pressure chamber 5 through the first opening 10 of the main body 2, crossed by the piston rod 7. The spacer 8 is sealed from both the chamber 5 and the environment by means of radial seal rings 35 positioned at both of its ends.

The device may optionally be provided with an actuator (not represented) for driving the piston rod 7 along the axis (A). The actuator is preferably a pneumatic actuator or an electric actuator, both being quite practical to use, contrary to, for example, a hydraulic actuator which requires a hydraulic system in order to work. The actuator is adapted so that the device can be sterilized and portable, and in particular, so that the device can be used under sterile conditions such as under a laminar flow hood.

The piston rod 7 is advantageously provided with a handle 9. In this way, the use of the piston rod 7 by an operator is made easier and more comfortable while at the same time the positioning of the piston rod along the main body 2 is more precise.

The stopper holder system 12 is configured to receive and hold a stopper 6 in a fixed position and aligned with the longitudinal axis (A) as well as with the direction of travel of the piston rod 7, prior to the positioning of said stopper 6 into the container 28. The stopper holder system is advantageously configured to maintain the stopper both axially and radially.

The stopper holder system 12 of the device 1 is located so as to be in communication with the chamber 5, and preferentially, inside the chamber 5.

In the embodiment of FIGS. 1, 2A, 2B, and 2C, the stopper holder system 12 is located more particularly at the distal end of the second portion 4 of the main body 2, in the vicinity of the second opening 11 of the main body. In this way, when held by the stopper holder system 12, the stopper 6 is located in the vicinity of the container 28 to be stoppered, thus reducing the travel path of the piston rod 7 wherein the piston rod contacts and pushes the stopper 6 into said container 28. Therefore, the stopper 6 does not have to move all along the chamber 5, which avoids providing drive or guide means for keeping the stopper aligned with the axis (A).

The stopper holder system 12 comprises a plurality of blocking elements 13. According to the embodiment illustrated in FIGS. 1 and 2A-B-C, and 3, the blocking elements 13 are arranged in a crown that extends around the second opening 11. The stopper holder system 12 is advantageously arranged so that the axis (A) passes through the center of the crown, thus allowing the piston rod 7 to pass through the center of the crown while pushing the stopper 6.

The blocking elements 13 extend parallel to the longitudinal axis (A) of travel of the piston rod 7 and are linked together by the wall 16 of the crown. They are advantageously mushroom-shaped, i.e. they comprise a stem 14 topped by an enlarged head 15. When the stopper 6 is positioned in the stopper holder system 12, the lateral wall of the stopper contacts the stems 14 of the blocking elements 13, and the proximal end of the stopper 6 abuts the head 15 of the blocking elements 13. Therefore, when the pressure in the variable pressure chamber 5 decreases below the atmospheric pressure, thus inducing the stopper 6 to be attracted in a proximal direction due to the pressure differential between the pressure in the chamber 5 and the pressure in the container 28, the stopper 6 abuts the head 15 of the blocking elements 13, and is prevented from moving proximally into the chamber 5. Therefore, the stopper 6 remains in position in the stopper holder system 12 until being pushed on by the piston rod 7. The stems 14, surrounding the stopper 6, maintain the stopper radially. Said stems 14 may be configured to compress the stopper radially so as to further improve axial and radial blocking of the stopper.

Moreover, the stopper holder system 12 is configured so as to define with respect to the stopper 6 at least an air-circulating passage 17 when said stopper 6 is positioned in the stopper holder system 12. In this way, air can flow from one side of the stopper holder system 12 to the other side.

When the stopper 6 is positioned in the stopper holder system 12, the borders of the head 15 of the blocking elements 13, the wall 16 of the crown and the stopper 6 define the air-circulating passage 17 for air to flow through from the chamber 5 into the container 28 and vice versa.

When the vacuum is pulled in the chamber 5, the air is flowing in a proximal direction from the inside of the container 28 to the vacuum pump 30 (shown on FIG. 4) through the air-circulating passages 17 and the chamber 5. When the vacuum is broken, the air is flowing in a distal direction from the vacuum pump 30 to the container 28 through the chamber 5 and the air-circulating passages 17.

Figure 4:
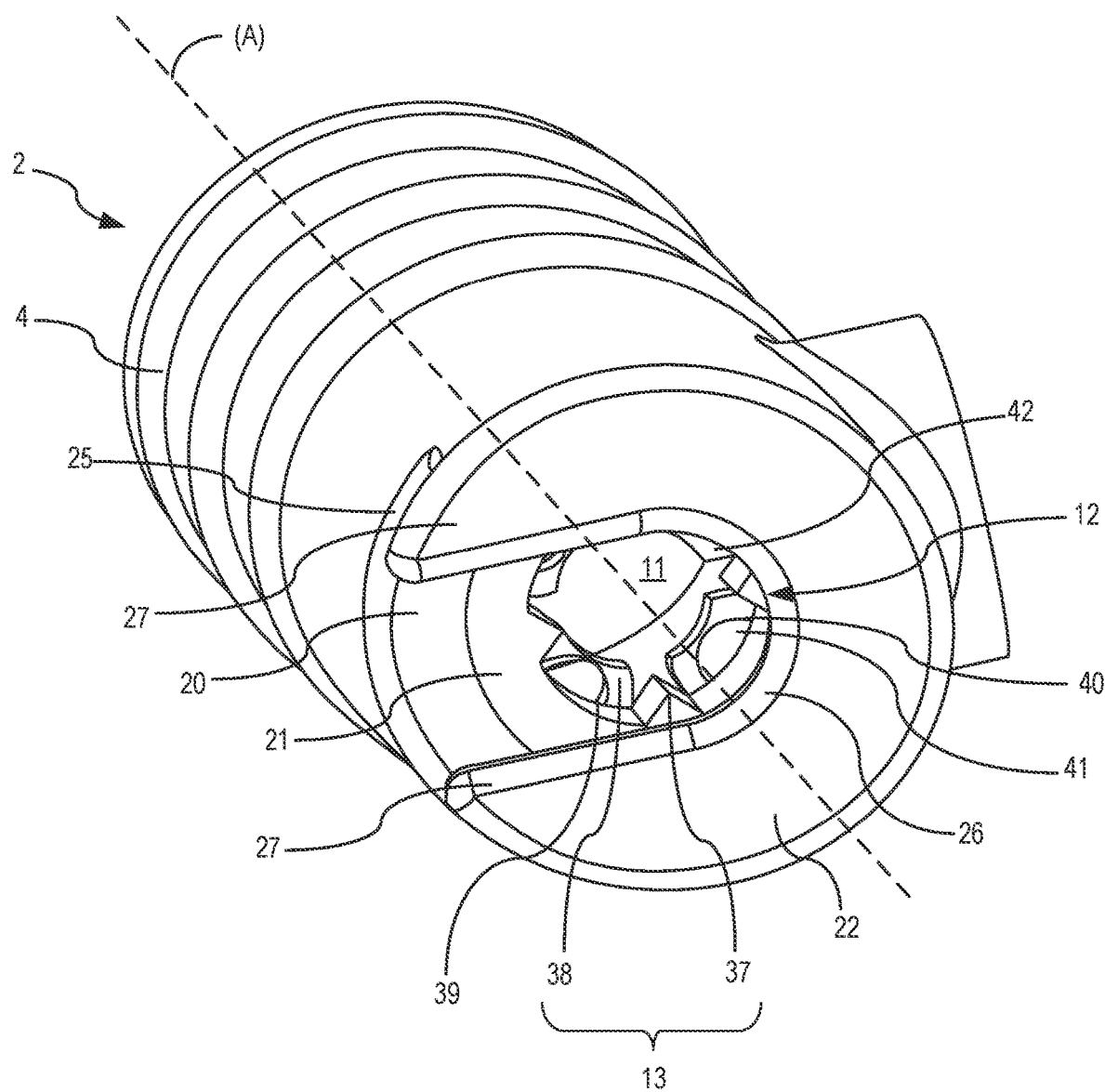
FIG. 4 is a perspective view of another embodiment of the stopper holder system of the device.

Another embodiment of the stopper holder system 12 is illustrated on FIG. 4. The stopper holder system of this embodiment is positioned in the same location as the stopper holder system of the embodiment of FIGS. 1, 2A, 2B, 2C, and 3.

According to FIG. 4, the stopper holder system 12 comprises two sets of blocking elements, including a first set 37 and a second set 38 of blocking elements respectively arranged in two concentric crowns that extend around the second opening 11. The stopper holder system 12 is advantageously arranged so that the longitudinal axis (A) passes through the center of the crowns, thus allowing the piston rod 7 to pass through the center of the crowns while pushing the stopper 6.

Concerning the first set of blocking elements 37, the blocking elements form angular parts, preferably triangular parts, that extend radially (i.e. in a direction perpendicular to the axis (A)) from the wall 39 of the first crown that connects each angular part to an adjacent one.

Concerning the second set of blocking elements 38, the blocking elements form bearing parts that extend radially from the wall 40 of the second crown that connects each bearing part to an adjacent one, and are regularly spaced from each other along the wall 40. Each bearing part 38 includes at least one perforation 41 that extends axially (i.e. in a direction parallel to the axis (A)) through the bearing part. Moreover, the perforations 41 of the bearing parts 38, that can be partially covered by the stopper 6 when the latter is positioned in the stopper holder system 12, serve as air-circulating passage for air to flow through from the chamber 5 into the container 28 and vice versa. The angular parts 37 are advantageously offset from the bearing parts 38 to provide a better air flow. The function of such air-circulating passage has been already discussed earlier for the previous embodiment of the stopper holder system 12.

When the stopper 6 is positioned in the stopper holder system 12, the lateral wall of the stopper 6 is in contact with the apices of the angular parts 37 and the proximal end of the stopper 6 abuts the bearing parts 38. Therefore, when the pressure in the variable pressure chamber 5 decreases below the atmospheric pressure, thus inducing the stopper 6 to be attracted in the proximal direction due to the pressure differential ΔP (difference between the pressure $P_0$, typically atmospheric pressure of the environment surrounding the medical container 27, and the pressure $P_1$ inside the device after mechanical positioning of the stopper under vacuum) the stopper 6 abuts the bearing parts 38 and is prevented from moving proximally into the chamber 5. The stopper 6 thus remains in position in the stopper holder system 12 until being pushed on by the piston rod 7. The angular parts 37, surrounding the stopper 6, maintain the stopper radially. Said angular parts 37 may be configured to compress the stopper radially so as to further improve axial and radial blocking of the stopper.

The inner parts 42 of the bearing parts 38 are preferably curved so that the curvature of the bearing parts 38 form an inner circle that corresponding substantially to the shape of the piston rod 7. Of course, the dimensions of the bearing parts 38 and of the angular parts 37 are adapted to provide an axial blockage of the stopper 6 and to allow the displacement of the piston rod 7 through the stopper holder system 12 in order to push the stopper 6.

The embodiment of FIG. 4 is particularly preferred for smaller stoppers, e.g. stoppers for containers having a volume less than 5 ml.

Of course, the injection device may comprise other embodiments of the stopper holder system, without departing from the scope of the invention. For example, the stopper holder system may comprise a plurality of blocking elements having a curved surface which is configured to compress the stopper radially.

As mentioned previously, the stopper holder system 12 allows maintaining the stopper 6 in a position before it is introduced into the container wherein the stopper is substantially aligned with the axis (A) of travel of the piston rod 7. When the piston rod is pushed in a distal direction, the piston rod 7 collides with the stopper 6 and then pushes said stopper in a distal direction into the container 28, through the proximal end of the container.

The container holder system 18 of the device is configured to receive the proximal end of the container 28 to be stoppered. The container holder system 18 is located distally relative to the stopper holder system 12, and is configured to maintain the container 28 in a position substantially aligned with the axis (A) of travel of the piston rod 7, so that when moving in a distal direction, the piston rod 7 pushes the stopper 6 previously positioned in the stopper holder system 12 into the container 28.

In a general way, the container holder system 18 is configured so that, when the container 28 is received in the container holder system, the proximal end of the container faces and contacts axially a surface of the container holder system. In that way, the surface of the container holder system closes the proximal end of the container, thereby providing an effective sealing of the device by avoiding any air leak between the device and the environment.

According to the embodiment of FIGS. 1 and 2A-B-C, the container holder system 18 is located at the distal end of the second portion 4 of the main body 2, in the vicinity of the stopper holder system 12, thus minimizing the distance between the stopper 6 positioned in the stopper holder system 12 and the container 28. This allows for reducing the travel path of the piston rod 7 wherein the piston rod contacts and pushes the stopper 6 in a distal direction into said container 28, for the reasons explained above.

The container holder system 18 comprises a proximal wall 19, a distal wall 22 that faces the proximal wall, and a lateral wall 23 joining the proximal and distal walls. The proximal wall 19, the distal wall 22, and the lateral wall 23 define a housing 24 configured to receive the proximal end of the container 28 to be stoppered.

The container holder system 18 allows for maintaining the container 28 inserted herein in a fixed position, as well as securing the container by preventing it from falling off from the device 1 while the stopper 6 is being positioned into the container.

According to the embodiment of FIGS. 1 and 2A-B-C, the proximal wall 19 comprises a border 20 that surrounds a recess 21, said recess corresponding to the distal end of the second portion 4 of the main body. A seal or suction cup (not represented on the Figures) is positioned in the recess 21, so as to extend between the second opening 11 and the border 20. The seal avoids any air leak between the device and the environment, and can be made of any adapted material such as rubber for example. The seal is advantageously an O-ring or could be flat.

When in position in the container holder system 18, the proximal end of the container 28 is inserted in the recess 21 and contacts the seal thus preventing any leak when the vacuum is pulled and covers the second opening 11 of the main body 2. The container 28 is also aligned with the second opening 11 and, as a result, with the longitudinal axis (A) of travel of the piston rod 7.

Moreover, from a practical point of view, when the vacuum is pulled in the chamber 5 to a pressure $P_1$ inferior to the atmospheric pressure $P_0$, the container 28 which is pulled by the vacuum forces towards the proximal direction and as a result pressed against the proximal wall 19.

The lateral wall 23 is provided with a slot 25, and the distal wall 22 is provided with a through groove 26 continuous with the slot 25, said groove extending from the slot through the distal wall 22. In a practical way, the proximal end of the container 28 is inserted through the slot 25 of the lateral wall, and moved in a radial direction along the groove 26 of the distal wall until the container 28 is aligned with the second opening 11 of the main body 2. The proximal end of the container 28 is then moved upwards against the seal located into the recess 21.

The groove 26 is configured to allow the insertion of the container 28 while avoiding said container to fall off the device. To this end, the width of the groove 26 is advantageously smaller than the width of the proximal end of the container 28.

The groove 26 is configured so that the inner surface of the groove contacts the body of the container 28. In particular, the groove 26 can be configured to prevent the container 28 inserted herein from moving radially, unless the container is moved by an operator. The groove is preferably made of a rigid and smooth material, such as rigid plastic or metal (aluminum, stainless steel) for example, for making the insertion of the container therein easier, as well as contributing to maintain the container in a fixed position in the housing 24 while the container is being stoppered.

To this end, the groove 26 can comprise adjustment means for adjusting the width of the groove.

For the same purpose, the structure of both the slot 25 and the groove 26 may be adapted according to the type of container 28 intended to be stoppered by the device 1.

When the container 28 is a syringe or the like for example, as the width of the proximal end of the container 28 is greater than the width of its body, the width of the slot 25 is greater than the width of the groove 26. This configuration is the one represented in the embodiment of FIGS. 1 and 2A-B-C. The entrance of the groove 26 is delimited by two projecting parts 27 formed in the distal wall, that face the proximal wall. In this configuration, when inserted in the groove 26, the proximal end of the container 28 can abut the projecting parts 27 thus preventing the container from falling off the groove.

Alternatively, when the container 28 is a cylinder or the like, as the width of the cylinder is the same all along its length, the width of the slot 25 can be the same as the width of the groove 26. In this configuration, the proximal end of the container 28 cannot abut the distal wall 22, but the container 28 can still be maintained in the groove 26 if said groove is configured to prevent the container 28 inserted herein from moving radially and as described previously.

The seal can be adapted according to the type of container 28 as well. For example, when the container is a syringe or the like, the seal can be a flat seal, whereas when the container is a cylinder, the seal can be an o-ring seal.

Contrary to prior art vacuum stoppering apparatuses that do not comprise any container holder system (the container being merely placed in alignment with the piston rod), the container holder system of the device according to the invention is attached to the body; thus, the container is fixed to the main body during use. This contributes, along with the general structure of the device having reduced dimensions and weight, to make the device handheld and easy to carry for use, especially for performing quick and simple implementation of vacuum stoppering of a medical container. Besides, the device—either as a whole or only the second portion 4, i.e. the part of the device which is likely to be in contact with the composition contained in the container—can be easily sterilized in an autoclave.

The device is handheld, which means it can be carried in one hand of a user during use and transport from one location to another. The dimensions and weight of the device are advantageously adapted for this purpose. For example, the main body 2 preferably has a length comprised between 20 centimeters and 30 centimeters, a weight inferior to 1 kilogram, more preferably comprised between 50 grams and 300 grams, and a diameter comprised between 5 centimeters and 10 centimeters.

When using the device, the user can hold the main body in a substantially vertical position with one hand while mounting the medical container in the container holder system with the other hand. Then, for pulling the vacuum in the device, the user may keep gripping the main body with one hand, and pull then adjust the vacuum with the vacuum pump 30 and the vacuum valve 31 respectively with the other hand, before pushing the piston rod 7 with said other hand. If necessary, the device may of course be fixed onto an appropriate device so as to facilitate the process, such as a hanger arm for example.

In a preferred embodiment of the device, the first portion 3 including the spacer 8, and the second portion 4 including the variable pressure chamber 5, the stopper holder system 12, and the container holder system 18, are separable from each other. In other terms, the first and second portions 3, 4 can be selectively connected to each other when the device 1 is to be used, or separated from each other otherwise. The piston rod 7 can preferably also be separated from the first portion 3 of the device.

Hence, for a given implementation of vacuum stoppering of a medical container 28, it is possible to sterilize only the second portion 4 of the device, and to reuse the first portion 3 previously sterilized, without having to sterilize it again. Same goes for the piston rod 7 when said piston rod was sterilized with the first portion prior to the implementation.

A threaded connection or a snap-fit connection, for example, are particularly adapted for connecting and separating the first and second portions 3, 4 of the device. The first portion and the second portion can alternatively be connected by other suitable connections, provided that sufficient tightness can be achieved, for example with further positioning of a seal on the connection.

Moreover, the device 1 can comprise at least two second portions 4, each second portion comprising a container holder system 18 configured to receive an end of a medical container 28 of a different size.

Hence, it is possible to adapt the device 1 to suit a container 28 of any given size with a plurality of removable second portions 4 whose container holder systems 12 match the size of the containers 28.

Figure 5:
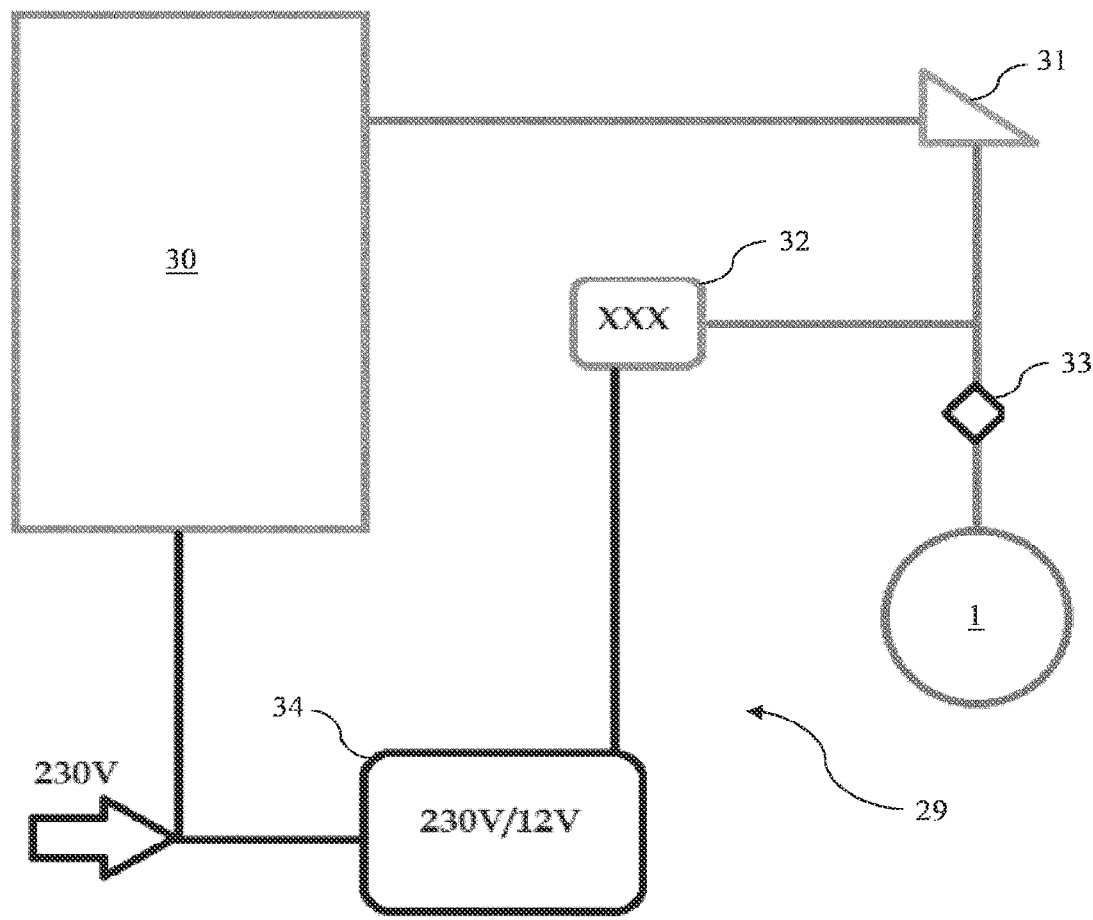
FIG. 5 is a schematic representation of a system comprising the device of the invention.

Another object of the invention is a system 29 for vacuum stoppering a medical container 28 comprising a device 1 as previously described, and a method of vacuum-stoppering a container 28 using such device 1 or system 29. The process will be further explained along with the system illustrated in FIG. 5.

The system 29 comprises the device 1, a vacuum pump 30, a micrometric or any other type of vacuum valve 31, a back valve 33, a pressure probe (not represented) connected to a digital display 32, and a power source 34.

First, a stopper 6 is positioned in the stopper holder system 12 of the device 1, under atmospheric pressure $P_0$. The container 28, previously filled with a composition, is then positioned in the container holder system 18 of said device 1. At this time, the piston rod 7 is in a rest position. If not done already, the variable pressure chamber 5 is connected to the vacuum pump 30 via the outlet 36. The vacuum is then pulled in the chamber 5 until the pressure reaches a predetermined pressure $P_1$, inferior to the atmospheric pressure $P_0$. The pressure is adjusted by means of a micrometric vacuum valve 31 that can be manually handled, and the pressure in the chamber 5 can be check via a digital display 32 that receives pressure measures from a probe positioned inside the chamber 5 or in the vacuum line. The container 28 is pulled in a proximal direction against the device 1 directly by the vacuum forces or in a first step by the operator, whereas the stopper 6 remains in position in the stopper holder system 12.

Once the pressure read on the display 32 matches the predetermined pressure $P_1$, the piston rod 7 is pushed in a distal direction along the axis (A) to an operative position wherein said piston rod pushes the stopper 6 in a distal direction from the stopper holder system 12, up to the inside the container 28. The piston rod 7 is then moved pulled in a proximal direction, back to the rest position.

Note that the position of the stopper 6 inside the container 28 does not need to be precise, as long as the stopper 6 is not positioned too close to the proximal end of the container 28.

Then, breaking the vacuum by means of the back valve 33 increases the pressure inside the chamber 5, and causes the stopper 6 to move further down the container 28 to the surface of the composition: the container is then stoppered.

In more details, the stopper 6 is moving down by itself, with no help from the piston rod 7. Indeed, the pressure in the portion of container between the stopper 6 and the surface of the composition is equal to $P_1$, while the pressure in the other side of the stopper is increasing. The pressure differential causes the stopper 6 to move in the distal direction until pressure equilibrium is reached, which corresponds to a position of the stopper 6 wherein the latter is right above the surface of the composition.

Thanks to the device 1, the elements of the method can be carried out manually by an operator. For example, the operator can:
1) Manually position the stopper 6 in the stopper holder system 12 of the device 1,
2) Position the container 28 in the container holder system 18 of the device 1, and
3) Push the piston rod 7 in a distal direction so as to position the stopper 6 inside the medical container 28.

This allows for carrying out quick and simple implementation of vacuum stoppering of a medical container, in any kind of environmental conditions such as cleanrooms, sterile environment or uncontrolled environment and switch from one to another easily.

What is claimed is:

1. A device for vacuum stoppering a medical container, comprising:
    a main body having a proximal end, a distal end, and a sidewall defining an internal volume comprising a variable pressure chamber configured to be connected to a vacuum pump;
    a stopper holder system arranged in communication with the variable pressure chamber, wherein the stopper holder system comprises at least one blocking element that receives and holds a stopper in a fixed position relative to the main body and prevents movement of the stopper in a proximal direction within the main body;
    a piston rod moveable inside the internal volume of the main body along a longitudinal axis between a proximal rest position wherein the piston rod is remote from the stopper and a distal operative position wherein the piston rod contacts and pushes the stopper; and
    a container holder system, arranged distally relative to the stopper holder system and in communication with the variable pressure chamber, the container holder system being configured to receive an end of a medical container and to hold the medical container aligned with a direction of travel of the piston rod such that movement of the piston rod pushes the stopper from the stopper holder system into the medical container.

2. The device according to claim 1, wherein the main body comprises a first portion including a spacer that guides the piston rod along the longitudinal axis, and a plurality of second portions selectively and removably connectable to a distal end of the first portion, and each of the plurality of second portions includes the variable pressure chamber, the stopper holder system, and the container holder system and is sized for connection to and stoppering of a medical container of a different size.

3. The device according to claim 1, wherein the container holder system comprises:
    a proximal wall provided with an opening in communication with the variable pressure chamber, the opening being aligned with the longitudinal axis of the piston rod, such that, during movement of the piston rod, the piston rod passes through the opening;
    a distal wall facing the proximal wall and joined to the proximal wall by a lateral wall provided with a slot extending through a first portion of the circumference of the lateral wall and a groove on an interior surface continuous with the slot extending around a second portion of the circumference of the lateral wall; and
    the proximal wall, the distal wall, and the lateral wall defining a housing that receives the end of the medical container when the medical container is inserted into the slot and then moved along the groove.

4. The device according to claim 3, wherein the proximal wall of the container holder system further comprises a recess that contacts the end of the medical container and blocks the medical container radially when the medical container is positioned in the housing and the variable pressure chamber is under vacuum.

5. The device according to claim 1, wherein the stopper holder system comprises a plurality of blocking elements arranged on a circular wall, the stopper holder system being arranged such that, during movement of the piston rod, the piston rod passes through a center of the circular wall and pushes the stopper away from the blocking elements.

6. The device according to claim 5,
    wherein each blocking element comprises a stem topped by a proximal enlarged head, and each blocking element is connected to an adjacent blocking element by the circular wall, and
    wherein when the stopper is in the fixed position, the stopper is in contact with the stems of the blocking elements and blocked in the proximal direction by the heads of the blocking elements, and the stopper defines, with the blocking elements and the circular wall, a plurality of air-circulating passages.

7. The device according to claim 5, wherein the stopper holder system comprises:
    a first set of blocking elements arranged on a first circular wall and a second set of blocking elements arranged on a second circular wall,
    wherein each blocking element of the first set of blocking elements is connected to an adjacent blocking element by the first circular wall, and each blocking element of the second set of blocking elements is connected to an adjacent blocking element by the second circular wall,
    the blocking elements of the first set form angular parts that extend radially from the first circular wall,
    the blocking elements of the second set form bearing surfaces that extend radially from the second circular wall, each bearing part including at least one perforation, and
    when the stopper is in the fixed position, the stopper is in contact with apexes of the angular parts and blocked in the proximal direction by the bearing parts, and the perforations of the bearing parts provide fluid communication between the variable pressure chamber and the container.

8. The device according to claim 1, wherein the stopper holder system fixes the stopper in both an axial direction and a radial direction.

9. A device for vacuum stoppering a medical container, comprising:
    a main body comprising a first portion and a plurality of second portions selectively and removably connectable to a distal end of the first portion,
    wherein the main body defines an internal volume,
    each of the second portions comprises:
        a variable pressure chamber defined in the internal volume;
        a stopper holder system arranged in communication with the variable pressure chamber, wherein the stopper holder system comprises at least one blocking element that receives and holds a stopper in a fixed position relative to the main body;
a piston rod moveable inside the internal volume of the main body along a longitudinal axis between a proximal rest position wherein the piston rod is remote from the stopper and a distal operative position wherein the piston rod contacts and pushes the stopper; and
a container holder system, arranged distally relative to the stopper holder system and in communication with the variable pressure chamber, the container holder system being configured to receive an end of a medical container and to hold the medical container aligned with a direction of travel of the piston rod such that movement of the piston rod pushes the stopper from the stopper holder system into the medical container, and
each of the plurality of second portions is sized for connection to and stoppering of a medical container of a different size.

10. The device of claim 9, wherein the device further comprises a spacer that guides the piston rod along the longitudinal axis positioned in the internal volume of the first portion.

11. The device according to claim 9, wherein the container holder system comprises:
a proximal wall provided with an opening in communication with the variable pressure chamber, the opening being aligned with the longitudinal axis of the piston rod, such that, during movement of the piston rod, the piston rod passes through the opening;
a distal wall facing the proximal wall and joined to the proximal wall by a lateral wall provided with a slot extending through a first portion of the circumference of the lateral wall and a groove on an interior surface continuous with the slot extending around a second portion of the circumference of the lateral wall; and
the proximal wall, the distal wall, and the lateral wall defining a housing that receives the end of the medical container when the medical container is inserted into the slot and then moved along the groove.

12. The device according to claim 11, wherein the proximal wall of the container holder system further comprises a recess that contacts the end of the medical container and blocks the medical container radially when the medical container is positioned in the housing and the variable pressure chamber is under vacuum.

13. The device according to claim 9, wherein the stopper holder system comprises a plurality of blocking elements arranged on a circular wall, the stopper holder system being arranged such that, during movement of the piston rod, the piston rod passes through a center of the circular wall and pushes the stopper away from the blocking elements.

14. The device according to claim 13,
wherein each blocking element comprises a stem topped by a proximal enlarged head, and each blocking element is connected to an adjacent blocking element by the circular wall, and
wherein when the stopper is in the fixed position, the stopper is in contact with the stems of the blocking elements and blocked in the proximal direction by the heads of the blocking elements, and the stopper defines, with the blocking elements and the circular wall, a plurality of air-circulating passages.

15. The device according to claim 13, wherein the stopper holder system comprises:
a first set of blocking elements arranged on a first circular wall and a second set of blocking elements arranged on a second circular wall,
wherein each blocking element of the first set of blocking elements is connected to an adjacent blocking element by the first circular wall, and each blocking element of the second set of blocking elements is connected to an adjacent blocking element by the second circular wall,
the blocking elements of the first set form angular parts that extend radially from the first circular wall,
the blocking elements of the second set form bearing surfaces that extend radially from the second circular wall, each bearing part including at least one perforation, and
when the stopper is in the fixed position, the stopper is in contact with apexes of the angular parts and blocked in the proximal direction by the bearing parts, and the perforations of the bearing parts provide fluid communication between the variable pressure chamber and the container.

16. The device according to claim 9, wherein the stopper holder system fixes the stopper in both an axial direction and a radial direction.

17. A device for vacuum stoppering a medical container, comprising:
a main body defining an internal volume comprising a variable pressure chamber configured to be connected to a vacuum pump;
a piston rod moveable inside the internal volume of the main body along a longitudinal axis between a proximal rest position wherein the piston rod is remote from a stopper and a distal operative position wherein the piston rod contacts and pushes the stopper into the medical container;
a stopper holder system arranged in communication with the variable pressure chamber and configured to receive and hold the stopper in a fixed position relative to the main body and aligned with the direction of travel of the piston rod; and
a container holder system, arranged distally relative to the stopper holder system and in communication with the variable pressure chamber, the container holder system being configured to receive an end of a medical container and to hold the medical container aligned with the direction of travel of the piston rod such that movement of the piston rod from the proximal rest position to the distal operative position pushes the stopper from the stopper holder system into the medical container,
wherein the container holder systems comprises:
a proximal wall provided with an opening in communication with the variable pressure chamber, the opening being aligned with the longitudinal axis of the piston rod, such that, during movement of the piston rod, the piston rod passes through the opening;
a distal wall facing the proximal wall and joined to the proximal wall by a lateral wall provided with a slot extending through a first portion of the circumference of the lateral wall and a groove on an interior surface continuous with the slot extending around a second portion of the circumference of the lateral wall; and
the proximal wall, the distal wall, and the lateral wall defining a housing that receives the end of the medical container when the medical container is inserted into the slot and then moved along the groove.

18. The device according to claim 17, wherein the proximal wall of the container holder system further comprises a recess that contacts the end of the medical container and blocks the medical container radially when the medical container is positioned in the housing and the variable pressure chamber is under vacuum.

19. The device according to claim 17, wherein the stopper holder system comprises a plurality of blocking elements arranged on a circular wall, the stopper holder system being arranged such that, during movement of the piston rod, the piston rod passes through a center of the circular wall and pushes the stopper away from the blocking elements.

20. The device according to claim 19,
wherein each blocking element comprises a stem topped by a proximal enlarged head, and each blocking element is connected to an adjacent blocking element by the circular wall, and
wherein when the stopper is in the fixed position, the stopper is in contact with the stems of the blocking elements and blocked in the proximal direction by the heads of the blocking elements, and the stopper defines, with the blocking elements and the circular wall, a plurality of air-circulating passages.

21. The device according to claim 19, wherein the stopper holder system comprises:
a first set of blocking elements arranged on a first circular wall and a second set of blocking elements arranged on a second circular wall,
wherein each blocking element of the first set of blocking elements is connected to an adjacent blocking element by the first circular wall, and each blocking element of the second set of blocking elements is connected to an adjacent blocking element by the second circular wall,
the blocking elements of the first set form angular parts that extend radially from the first circular wall,
the blocking elements of the second set form bearing surfaces that extend radially from the second circular wall, each bearing part including at least one perforation, and
when the stopper is in the fixed position, the stopper is in contact with apexes of the angular parts and blocked in the proximal direction by the bearing parts, and the perforations of the bearing parts provide fluid communication between the variable pressure chamber and the container.

22. The device according to claim 17, wherein the stopper holder system fixes the stopper in both an axial direction and a radial direction.

* * * * *